United States Patent [19]

Paust et al.

[11] 4,192,806
[45] Mar. 11, 1980

[54] METHYL FUMARALDEHYDE MONOACETALS AND PROCESS

[75] Inventors: Joachim Paust, Neuhofen; Horst Schumacher, Bobenheim am Berg, both of Fed. Rep. of Germany

[73] Assignee: Badische Anilin- & Soda-Fabrik Aktiengesellschaft, Fed. Rep. of Germany

[21] Appl. No.: 891,540

[22] Filed: Mar. 30, 1978

Related U.S. Application Data

[63] Continuation of Ser. No. 363,615, May 24, 1973, abandoned.

[30] Foreign Application Priority Data

May 26, 1972 [DE] Fed. Rep. of Germany ....... 2225612

[51] Int. Cl.$^2$ ............................................. C07D 319/04
[52] U.S. Cl. .................................................. 260/340.7
[58] Field of Search ...................... 260/340.7; 568/598

[56] References Cited

U.S. PATENT DOCUMENTS

| 2,729,650 | 1/1956 | Habeshaw et al. | 260/340.7 |
| 3,584,010 | 6/1971 | Riehen | 260/340.7 X |

OTHER PUBLICATIONS

Chem. Zentralblatt (1963), pp. 13138–13139.
M. S. Newman et al., JACS, 80 (1958), p. 6350.
S. W. Smith et al., JACS, 90 (1968), pp. 1249, 1253–1257
Leutner, Monatshefte d. Chem., 60 (1932), p. 345.
Patai, The Chemistry of Functional Groups (1967), pp. 332–335.
J. F. W. McOmie, Protective Groups in Organic Chemistry, Plenum Press, London and New York 1973, pp. 325–328.
Chem. Abstracts, vol. 63 (1965) 16210a.
Fieser et al., Reagents for Organic Synthesis (1967), pp. 142–143.
Fieser and Fieser, Reagents in Organic Chemistry (1961), pp. 471–472.

Primary Examiner—Ethel G. Love
Attorney, Agent, or Firm—Keil & Witherspoon

[57] ABSTRACT

Cyclic methyl fumaraldehyde monoacetals and a process for their production by oxidation of the corresponding methylbut-2-en-4-ol-1-al acetal with an $H_2SO_4$-containing solution of chromic acid in acetone. The new compounds are of considerable interest as intermediates in the synthesis of carotinoids.

9 Claims, No Drawings

METHYL FUMARALDEHYDE MONOACETALS AND PROCESS

This is a continuation of application Ser. No. 363,615 filed May 24, 1973, now abandoned.

This invention relates to cyclic methyl fumaraldehyde monoacetals of the formula I:

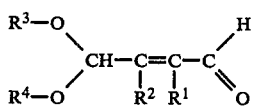

where $R^1$ and $R^2$ are different and denote hydrogen or methyl, and $R^3$ and $R^4$ together denote propylene which may bear $C_{1-4}$ alkyl, preferably methyl, as a substituent.

The invention also relates to a process for the production of the said acetals.

The new compounds are of considerable interest as intermediates in the synthesis of carotinoids. For example by reacting a 3-methylfumaraldehyde-1-acetal with the ylid of a β-ionylidene ethyl triphenylphosphonium salt followed by hydrolysis retinal is obtained in a simple manner which is in great demand and has hitherto been expensive to produce. An economic method of synthesizing β-carotene has thus become available. Furthermore, retinyl triphenylphosphonium salt obtained for example from retinol or vitamin A acetate can be elegantly converted into β-apo-$C_{25}$-carotinal by Wittig reaction with 2-methyl-fumaraldehyde-1-acetal followed by hydrolysis.

The new methyl fumaraldehyde monoacetals can be prepared in a fast and simple manner and in very high yields by oxidizing a methyl derivative of the corresponding but-2-en-4-ol-1-al acetal of the formula II:

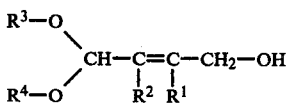

with a solution containing sulfuric acid of chromic acid in acetone.

The result is most surprising in that α,β-unsaturated acetals usually hydrolyze very rapidly in acid solution. Analogous chromic acid oxidation in a solution containing sulfuric acid using dimethyl or ethylene glycol acetals of the corresponding but-2-en-4-ol-1-als as starting materials is therefore unsuccessful. Examples of formula II compounds which may be oxidized to methyl fumaraldehyde monoacetals in this elegant manner are 2-methyl-but-2-en-4-ol-1-al(1',3'-propylene)acetal,
2-methyl-but-2-en-4-ol-1-al(2',4'-pentylene)acetal,
2-methyl-but-2-en-4-ol-1-al-(2',2'-dimethyl-propylene)-acetal,
3-methyl-but-2-en-4-ol-1-al-(1',3'-propylene)-acetal and
3-methyl-but-2-en-4-ol-1-al-(2',2'-dimethyl-propylene)-acetal.

The oxidation of the methyl derivatives of but-2-en-4-ol-1-al monoacetals and 2,3-diols using chromic acid in a solution containing sulfuric acid is usually carried out as follows.

The alcohol to be oxidized is dissolved in acetone and the $H_2SO_4$-containing solution of chromic acid added to this solution at a temperature of $-15°$ to $+30°$ C., preferably $-5°$ to $+20°$ C.

The acetone is generally used in such an amount that the alcohol to be oxidized is present in about 0.1 to 0.8 M, preferably 0.2 to 0.4 M, solution. Other solvents which are inert under the reaction conditions may be used, but the reaction then usually proceeds more slowly and not to completion. When using for example benzene as solvent, some 10% of the starting material remains behind unchanged even with a reaction period of 2 to 3 hours and using a 50% excess of oxidizing agent.

The $H_2SO_4$-containing solution of chromic acid may be for example Jones reagent which is about 8 N in chromic and sulfuric acids and is used in equivalent amounts. An excess of for example up to 50%, based on the amount theoretically required, of chromic and sulfuric acids may however also be used. It is convenient to use a solution which is 4 to 8 normal in chromic and sulfuric acids, preferably in an excess of 10 to 20% over the amount theoretically required.

The reaction mixture is worked up in conventional manner by pouring the reaction mixture into a similar amount of water, extraction with a solvent which is substantially immiscible with water and distillation.

By means of the process of the invention the methyl fumaraldehyde monoacetals which are of considerable interest for the synthesis of carotinoids can be prepared for the first time. The process is relatively easy to realize and usually proceeds with fairly good yields.

The invention will be further illustrated by the following Examples.

EXAMPLE 1

Manufacture of the starting materials (a) Acetalization of β-formyl crotyl acetate. A mixture of 142 g β-formyl crotyl acetate, 107 g neopentyl glycol, 0.2 g p-toluenesulfonic acid and 500 ml benzene is refluxed for three hours with azeotropic removal of water. The reaction mixture is allowed to cool, washed with sodium bicarbonate solution and dried over sodium sulfate. 216 g 2-methyl-4-acetoxy-but-2-en-1-al-1-(2',2'-dimethylpropylene) acetal boiling at 95° C. (0.1 mm) is obtained.

(b) Reaction with methanolic sodium methylate. A mixture of 228 g 2-methyl-4-acetoxy-but-2-en-1-al-1-(2',2'-dimethylpropylene) acetal, 5 ml of a 30% solution of sodium methylate in methanol and 250 ml methanol is heated at 450 mm and a bath temperature of 60° C., the methanol being distilled off. Another 150 ml methanol is then added and again distilled off. The residue is taken up in methylene chloride, washed with water and evaporated. 172 g 2-methyl-but-2-en-4-ol-1-al-(2',2'-dimethylpropylene)acetal boiling at 106° to 110° C. (0.4 mm) is obtained.

EXAMPLE 2

Oxidation of methylbut-2-en-4-ol-1-al acetal with chromic acid in a solution containing sulfuric acid A mixture of 15.2 g chromium trioxide and 23 g concentrated sulfuric acid, made up to 100 ml with water, is added at $+5°$ C. all at once to a solution of 37.2 g (0.2 mole) 2-methylbut-2-en-4-ol-1-al-(2',2'-dimethylpropylene)acetal in 1 l acetone. The reaction mixture is poured into 1 l (cold) water and extracted three times with 150 ml benzene. The benzene phases are washed with 5% sodium bicarbonate solution. Distillation of the combined benzene extracts gives 31.8 g 2-methyl-fumaraldehyde-1-(2',2'-dimethylpropylene)acetal. The yield is 85% of theory. B.P. 82° to 85° C. (0.1 mm).

NMR (δ [ppm] CDCl₃, TMS): 10.10 (d, 1H); 6.10 (m, 1H); 4.80 (S, 1H); 3.58 (m, 4H); 2.18 (S, 3H); 1.21 (S, 3H); 0.75 (S, 3H).

The methyl fumaraldehyde monoacetals named and characterized below are obtained in the yields specified by similarly reacting 0.2 mole of the corresponding methylbut-2-en-4-ol-1-al acetals.

2-methyl-fumaraldehyde-1(1',3'-propylene)-acetal

B.P. 80° C. (0.1 mm); Yield, 78% of theory.

NMR (δ [ppm], CDCl₃, TMS): 10.08 (d, 1H); 6.12 (d, 1H); 4.93 (S, 1H); 4.00 (m, 4H); 2.18 (S, 3H); 2.0–1.2 (m, 2H).

2-methyl-fumaraldehyde-1-(2',4'-pentylene)-acetal

B.P. 70° to 72° C. (0.2 mm); Yield, 75% of theory.

NMR (δ [ppm], CDCl₃, TMS): 10.08 (d, 1H); 6.17 (m, 1H); 4.95 (S, 1H); 4.1–3.6 (m, 2H); 2.18 (m, 3H); 1.6–1.2 (m, 2H); 1.24 (d, 6H).

3-methyl-fumaraldehyde-1-(2',2'-dimethylpropylene)-acetal

B.P. 85° to 87° C. (0.2 mm); 78% of theory.

NMR (δ [ppm], CDCl₃; TMS): 9.47 (S, 1H); 6.35 (m, 1H); 5.30 (d, 1H); 3.60 (m, 4H); 1.82 (d, 3H); 1.24 (S, 3H); 0.77 (S, 3H).

What we claim is:

1. Cyclic methyl fumaraldehyde monoacetals of the formula I

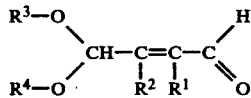

where $R^1$ and $R^2$ are different and denote hydrogen or methyl, and $R^3$ and $R^4$ together denote propylene or propylene having up to two $C_{1-4}$ alkyl substituents.

2. Monoacetals as claimed in claim 1 where the $C_{1-4}$ alkyl is methyl.

3. 2-methyl-fumaraldehyde-1-(1',3'-propylene)-acetal.

4. 2-methyl-fumaraldehyde-1-(2',4'-pentylene)-acetal.

5. 2-methyl-fumaraldehyde-1-(2',2'-dimethylpropylene)-acetal.

6. 3-methyl-fumaraldehyde-1-(2',2'-dimethylpropylene)-acetal.

7. A process for the production of methyl fumaraldehyde monoacetals of the formula I:

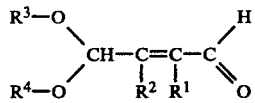

where $R^1$ and $R^2$ are different and denote hydrogen or methyl, and $R^3$ and $R^4$ together denote propylene or propylene having up to two $C_{1-4}$ alkyl substituents, wherein a methyl derivative of the corresponding but-2-en-4-ol-1-al acetal of the formula II:

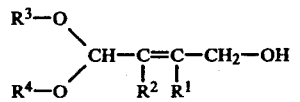

where $R^1$ to $R^4$ have the meanings given above is oxidized at temperatures of from −15° to +30° C. with a solution containing sulfuric acid and chromic acid in acetone.

8. A process as claimed in claim 7 wherein the solution used is 4 to 8 normal in chromic and sulfuric acids.

9. A process as claimed in claim 8 wherein said solution is used in an excess of 10 to 20% over the amount theoretically required.

* * * * *